(12) United States Patent
De Wilde et al.

(10) Patent No.: US 11,076,963 B2
(45) Date of Patent: Aug. 3, 2021

(54) REVISION GLENOID DEVICE

(71) Applicant: DePuy Synthes Products, Inc., Raynham, MA (US)

(72) Inventors: Lieven De Wilde, Ghent (BE); Kyle Lappin, Ft. Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 96 days.

(21) Appl. No.: 16/214,676

(22) Filed: Dec. 10, 2018

(65) Prior Publication Data
US 2019/0125542 A1 May 2, 2019

Related U.S. Application Data

(62) Division of application No. 14/027,907, filed on Sep. 16, 2013, now Pat. No. 10,172,715, which is a
(Continued)

(51) Int. Cl.
*A61F 2/40* (2006.01)
*A61B 17/16* (2006.01)
(Continued)

(52) U.S. Cl.
CPC ........ *A61F 2/4081* (2013.01); *A61B 17/1684* (2013.01); *A61F 2/30771* (2013.01); *A61B 17/1778* (2016.11); *A61B 17/86* (2013.01); *A61F 2002/3021* (2013.01); *A61F 2002/3069* (2013.01); *A61F 2002/3092* (2013.01);
(Continued)

(58) Field of Classification Search
CPC .............................................. A61F 2/40–4081
See application file for complete search history.

(56) References Cited

U.S. PATENT DOCUMENTS

| | | | |
|---|---|---|---|
| 2,487,203 A | 11/1949 | Wilber | |
| 3,855,638 A | 12/1974 | Pilliar | |

(Continued)

FOREIGN PATENT DOCUMENTS

| | | |
|---|---|---|
| CH | 693446 A5 | 8/2003 |
| EP | 1639949 A1 | 3/2006 |

(Continued)

OTHER PUBLICATIONS

Erichsen, "Injuries of the Nervous System on Railway and Other Injuries of the Nervous System", The Classic Article in Clinical Orthopaedics and Related Research, Mar. 1997, pp. 47-51, No. 458, Walton and Moberly, London (5 pages).

(Continued)

*Primary Examiner* — Marcia L Watkins
(74) *Attorney, Agent, or Firm* — Maginot, Moore & Beck LLP

(57) ABSTRACT

A glenoid component in one embodiment includes a base component with a planar upper circular rim defining a first plane, a receptacle opening to the first plane, a lower planar circular surface defining a second plane parallel to the first plane, and a conical outer wall extending from the upper circular rim to the lower planar circular surface. The glenoid component includes an articulating component with an upper articulating surface and a lower coupling portion configured to be inserted into the receptacle.

11 Claims, 8 Drawing Sheets

Related U.S. Application Data division of application No. 13/051,062, filed on Mar. 18, 2011, now Pat. No. 8,551,177.

(51) Int. Cl.
*A61F 2/30* (2006.01)
*A61B 17/17* (2006.01)
*A61B 17/86* (2006.01)
*A61F 2/46* (2006.01)

(52) U.S. Cl.
CPC ............ *A61F 2002/3093* (2013.01); *A61F 2002/30224* (2013.01); *A61F 2002/30331* (2013.01); *A61F 2002/30616* (2013.01); *A61F 2002/30617* (2013.01); *A61F 2002/30736* (2013.01); *A61F 2002/30769* (2013.01); *A61F 2002/30784* (2013.01); *A61F 2002/4677* (2013.01)

(56) References Cited

U.S. PATENT DOCUMENTS

| | | | |
|---|---|---|---|
| 4,030,143 | A | 4/1977 | Elloy et al. |
| 4,964,865 | A | 10/1990 | Burkhead et al. |
| 5,030,219 | A | 7/1991 | Matsen, III et al. |
| 5,080,673 | A | 1/1992 | Burkhead et al. |
| 5,180,384 | A | 1/1993 | Mikhail |
| 5,324,295 | A | 6/1994 | Shapiro |
| 5,489,310 | A | 2/1996 | Mikhail |
| 5,800,551 | A | 9/1998 | Williamson et al. |
| 5,919,195 | A | 7/1999 | Wilson et al. |
| 6,010,535 | A | 1/2000 | Shah |
| 6,045,302 | A | 4/2000 | Orr |
| 6,228,900 | B1 | 5/2001 | Shen et al. |
| 6,245,074 | B1 | 6/2001 | Allard et al. |
| 6,281,264 | B1 | 8/2001 | Salovey et al. |
| 6,364,910 | B1 | 4/2002 | Shultz et al. |
| 6,379,386 | B1 | 4/2002 | Resch et al. |
| 6,679,916 | B1 | 1/2004 | Frankle et al. |
| 6,699,269 | B2 | 3/2004 | Iannotti et al. |
| 6,783,549 | B1 | 8/2004 | Stone et al. |
| 7,294,133 | B2 | 11/2007 | Zink et al. |
| 7,329,284 | B2 | 2/2008 | Maroney et al. |
| 7,338,498 | B2 | 3/2008 | Long et al. |
| 7,604,665 | B2 | 10/2009 | Iannotti et al. |
| 8,764,836 | B2 | 7/2014 | De Wilde et al. |
| 2003/0125809 | A1 | 7/2003 | Iannotti et al. |
| 2004/0097947 | A1 | 5/2004 | Wolford et al. |
| 2004/0193168 | A1 | 9/2004 | Long et al. |
| 2005/0278030 | A1 | 12/2005 | Tornier et al. |
| 2006/0015112 | A1 | 1/2006 | McGovern |
| 2006/0020344 | A1 | 1/2006 | Shultz et al. |
| 2006/0069443 | A1* | 3/2006 | Deffenbaugh ........ A61F 2/4081 623/19.11 |
| 2006/0069444 | A1 | 3/2006 | Deffenbaugh |
| 2006/0111787 | A1 | 5/2006 | Bailie et al. |
| 2006/0195194 | A1 | 8/2006 | Gunther |
| 2006/0276905 | A1 | 12/2006 | Calamel |
| 2007/0016304 | A1 | 1/2007 | Chudik |
| 2007/0038302 | A1 | 2/2007 | Shultz et al. |
| 2007/0055249 | A1 | 3/2007 | Jensen et al. |
| 2007/0251356 | A1 | 11/2007 | Tribby |
| 2007/0260321 | A1* | 11/2007 | Stchur ................... A61F 2/4081 623/19.11 |
| 2008/0306600 | A1 | 12/2008 | Huebner |
| 2009/0270863 | A1 | 10/2009 | Maisonneuve |
| 2009/0270865 | A1 | 10/2009 | Poncet et al. |
| 2009/0270993 | A1 | 10/2009 | Maisonneuve et al. |
| 2010/0070044 | A1 | 3/2010 | Maroney et al. |
| 2010/0087876 | A1 | 4/2010 | Gunther |
| 2010/0161065 | A1 | 6/2010 | Williams, Jr. et al. |
| 2010/0249938 | A1 | 9/2010 | Gunther et al. |
| 2010/0274359 | A1 | 10/2010 | Brunnarius et al. |
| 2010/0331990 | A1 | 12/2010 | Mroczkowski et al. |
| 2011/0012318 | A1 | 1/2011 | Northwood |
| 2011/0028977 | A1 | 2/2011 | Rauscher et al. |
| 2011/0035013 | A1 | 2/2011 | Winslow et al. |
| 2012/0089233 | A1 | 4/2012 | Capon et al. |
| 2012/0130499 | A1 | 5/2012 | Long |
| 2012/0191201 | A1* | 7/2012 | Smits .................. A61F 2/40 623/19.11 |
| 2013/0123930 | A1 | 5/2013 | Burt |

FOREIGN PATENT DOCUMENTS

| | | | |
|---|---|---|---|
| EP | 1815825 | A1 | 8/2007 |
| FR | 2704747 | A1 | 11/1994 |
| FR | 2940607 | A1 | 7/2010 |
| GB | 2406278 | A | 3/2005 |
| JP | H11127256 | A | 5/1990 |
| JP | 2003230584 | A1 | 8/2003 |
| WO | 2010150223 | A1 | 12/2010 |
| WO | 2011005205 | A1 | 1/2011 |

OTHER PUBLICATIONS

Iannotti JP, Gabriel JP, Schneck SL, Evans BG, Misra S., "The normal glenohumeral relationships. An anatomical study of one hundred and forty shoulders," J. Bone Joint Surg Am. 1992;74(4); 491-500, No doi found. (11 pages).

Karduna AR, Williams GR, Williams JL, Ianotti JP., "Glenohumeral Joint translations before and after total shoulder arthroplasty," J Bone Joint Surg 1997;79-A,1166-74. No doi found. (10 pages).

Lee SB, Kim KJ, O'Driscoll SW, Morrey BF, An KN., "Dynamic glenohumeral stability provided by the rotator cuff muscles in the mid-range and end-range of motion." A study in cadavera. J. Bone Joint Surg Am. 2000;82(6):849-57. No doi found (10 pages).

Lewis GS, Bryce CD, Davison AC, Hollenbeak CS, Piazza SJ, Armstrong AD., "Location of the optimized centerline of the glenoid vault: a comparison of two operative techniques with use of three-dimensional computer modeling." J Bone Joint Surg Am, 2010;92:1188-94. doi:10-2106/JBJS.I.00131. (8 pages).

Mahfouz M, Nicholson G, Komistek R, Hovis D, Kubo M., "In vivo determination of the dynamics of normal, rotator cuff-deficient, total, arid reverse replacement shoulders." J Bone Joint Surg Am. 2005;87 Suppl 2:107-13. doi:10.2106/JBJS.E.00483 (8 pages).

Massimini DF; Li G, Warner JP., "Glenohumeral contact kinematics in patients after total shoulder arthroplasty." J Bone Joint Surg Am. Apr. 2010;92(4):916-26. doi:10.2106/JBJS.H.01610, (12 pages).

Matsen FA., "Early effectiveness of shoulder arthroplasty for patients who have primary glenohumeral degenerative joint disease." J Bone and Joint Surg 1996;78-A:260-4. No doi found. (6 pages).

Nyffeler RW, Sheikh R, Atkinson TS, Jacob HA, Favre P, Gerber C., "Effects of gienoid component version on humeral head displacement and joint reaction forces: an experimental study." J Shoulder Elbow Surg. 2006:15:625-9, doi:10.1016/j.jse.2005.09.016. (5 pages).

Nyffeler RW, Werner CM, Sukthankar A, Schmid MR, Gerber C., "Association of a large lateral extension of the acromion with rotator cuff tears." J. Bone Joint Surg Am. 2006;88-800-5, No doi found (7 pages).

Pappas GP, Blemker SS, Beaulieu CF, McAdams TR, Whalen ST, Gold GE., "In vivo anatomy of the Neer and Hawkins sign positions for shoulder impingement." J Shoulder Elbow Surg 2006;15:40-9. doi:10.1016/j.jse.2005.04.007, (10 pages).

Pearl ML, Krurtz S., "Geometric analysis of commonly used prosthetic systems for proximal humeral replacement." J Bone Joint Surg 1999;81-A:660-71. No doi found (13 pages).

Scalise JJ, Codsi MJ, Bryan J, Brems JJ, Iannotti JP., "The influence of three-dimensional computed tomography images of the shoulder in preoperative planning for total shoulder arthroplasty." J Bone Joint Surg Am. 2008;90:2438-45.doi:10.2106/JBJS.G.01341. (9 pages).

Schiffern SC, Rozencwaig R, Antoniou J, Richardson ML, Matsen FA III., "Anteroposterior centering of the humeral head on the glenoid in vivo." Am J Sports Med. 2002;30(3):382-7, No doi found. (7 pages).

Soslowsky LJ, Flatow EL, Bigliani LU, Pawiuk RJ, Ateshian GA, Mow VC., "Quantitation of in situ contact areas at the glenohumeral

(56) References Cited

OTHER PUBLICATIONS joint: a biomechanical study." J Orthop Res. 1992;10:524-34. doi:10.1002/jor.1100100407. (11 pages).
Takase K, Yamamoto K, Imakiire A, Burkhead WZ Jr., "The radiographic study in the relationship of the glenohumeral joint." J Orthop Res. 2004;22:298-305. doi:10.1016/S0736-0266(03)00187-6 (8 pages).
Tokgoz N, Kanatli U, Voyvoda NK, Gultekin S, Bolukbasi S, Tali ET., "The relationship of glenoid and humeral version with supraspinatus tendon tears." Skeletal Radion. 2007;36:509-14. No doi found. (6 pages).
Werner CML, Weishaupt D, Blumenthal S, Curt A, Favre P, Gerber C., "Effect of experimental suprascapular nerve block on active glenohumeral translations in vivo." J Orthop Res 2006;24:491-500. doi:10.1002/jor.20011, (10 pages).
International Preliminary Report on Patentability in corresponding PCT application PCT/US2012/029034, dated Sep. 24, 2013 (7 pages).
Extended European Search Report corresponding to European Application No. 16167719.0-1654, dated Sep. 6, 2016 (16 pages).
Extended European Search Report corresponding to European Application No. 12760274.6, dated Jun. 27, 2014 (6 pages).
Extended Search Report corresponding to European Application No. 12760199.5, dated Aug. 7, 2014 (6 pages).
Australian Examination Report corresponding to application No. 2012231298, dated Sep. 17, 2015, (4 pages).
Chinese Search Report corresponding to application No. 201280023890.7, dated Jun. 5, 2015, (2 pages).
Japanese Office Action corresponding to application No. 2013-558132, dated Jan. 12, 2016 (5 pages).
Extended European Search Report corresponding to European Patent Application 12760666.3, dated May 13, 2014 (10 pages).
Middernacht et al., "Consequences of Scapular Anatomy for Reversed Total Shoulder Arthroplasty," Clinical Orthopedics and Related Research (2008) 466:1410-1418 (9 pages).
Piasecki et al. Review Article: "Glenoid Bone Deficiency in Recurrent Anterior Shoulder Instability: Diagnosis and Management," J Am Acad. Ortho. Surg. 2009, vol. 17, pp. 482-493 (12 pages).
Jeske, H.C. et al., "Normal Glenoid Rim Anatomy and the Reliability of Shoulder Instability Measurements Based on Intrasite Correlation," Surg. Radiol. Anat., vol. 31, pp. 623-625. Mar. 2009 (3 pages).
Bey, Michael J., et al., "Measuring Dynamic In-Vivo Glenohumeral Joint Kinematics: Technique and Preliminary Results," Journal of Biomechanics 41 (2008), pp. 711-714. (4 pages).
Chant, Chris B., et al., "Humeral Head Retroversion in Competitive Baseball Players and Its Relationship to Glenohumeral Rotation Range of Motion," Journal of Orthopaedic & Sports Physical Therapy, Sep. 2007, vol. 37, No. 9, pp. 514-520. (7 pages).
Conzen, Annemarie and Eckstein, Felix, MD, "Quantitative Determination of Articular Pressure in the Human Shoulder Joint," Journal of Shoulder and Elbow Surgery, vol. 9, No. 3, May/Jun. 2000, pp. 196-204. (9 pages).
De Wilde, Lieven F. MD, et al., "Glenohumeral Relationship in the Transverse Plane of the Body," Journal of Shoulder and Elbow Surgery, vol. 12, No. 3, May/Jun. 2003, pp. 260-267. (8 pages).
De Wilde, L.F., et al., "About the Variability of the Shape of the Glenoid Cavity," Surgical and Radiologic Anatomy :2004) 26; pp. 54-59. (6 pages).
Fleiss, Joseph L., "Analysis of Data From Multiclinic Trials," Controlled Clinical Trials 7: 267-275 (1986). (9 pages).
Hertel, Ralph M.D., "Geometry of the Proximal Humerus and Implications for Prosthetic Design," Journal of Shoulder and Elbow Surgery, Jul./Aug. 2002, vol. 11, No. 4, pp. 331-338. (8 pages).
Mansat, M. and Fourcade, D., "Preoperative Planning in Shoulder Prosthesis," Acta Orthopaedica Belgica (1995) vol. 61—Suppl. 1-1995. (6 pages).
Middernacht, Bart, MD, et al., "Consequences of Scapular Anatomy for Reversed Total Shoulder Arthroplasty," Clinical Orthopaedics and Related Research (2008) 466: 1410-1418. (9 pages).

Moon, P. and Spencer, D.E., Rectangular Coordinates (x,y,z). Field Theory Handbook, Including Coordinate Systems, Differential Equations, and Their Solutions (1988), New York: Springer-Verlag, pp. 9-11 (Table 1.01). (3 pages).
Pearl, Michael L., M.D. and Volk, Albert G., M.D., "Corona Plane Geometry of the Proximal Humerus Relevant to Prosthetic Arthroplasty," Journal of Shoulder and Elbow Surgery, vol. 5, No. 4, Jul./Aug. 1996, pp. 320-326. (7 pages).
Pearl, ML and Volk, AG, "Retroversion of the Proximal Humerus in Relationship to Prosthetic Replacement Arthroplasty," Journal of Shoulder and Elbow Surgery, Jul. 1995, vol. 4, No. 4, pp. 286-289. (4 pages).
Randelli, M., M.D. and Gambrioli, P.L., M.D., "Glenohumeral Osteometry by Computed Tomography in Normal and Unstable Shoulders," Clinical Orthopaedics and Related Research, No. 208, Jul. 1986, pp. 151-156. (6 pages).
Robertson, Douglas D., M.D., et al., "Three-Dimensional Analysis of the Proximal Part of the Humerus: Relevance to Arthroplasty," The Journal of Bone and Joint Surgery, vol. 82-A,No. 11, Nov. 2000, pp. 1594-1602. (9 pages).
Rougraff, Bruce T., M.D., et al., "Does Length of Symptoms Before Diagnosis of Sarcoma Affect Patient Survival?" Clinical Orthopaedics and Related Research (2007), No. 462, pp. 181-189. (9 pages).
Shrout, Patrick E. and Fleiss, Jospeh L., "Intraclass Correlations: Uses in Assessing Rater Reliability," Psychological Bulletin, 1979, vol. 86, No. 2, pp. 420-428. (9 pages).
Soslowsky, Louis J., Ph.D. et al, "Articular Geometry of the Glenohumeral Joint," Clinical Orthopaedics and Related Research, No. 285, Dec. 1992, pp. 181-190. (10 pages).
Tetreault, Patrice, et al., "Glenoid Version and Rotator Cuff Tears," Journal of Orthopaedic Research 22 (2004) pp. 202-207. (6 pages).
Warner, Jon J.P., M.D. et al, "Articular Contact Patterns of the Normal Glenohumeral Joint," Journal of Shoulder and Elbow Surgery, Jul./Aug. 1998, vol. 7, No. 4, pp. 381-388. ( 8 pages).
Westerhoff, P., et al., "In Vivo Measurement of Shoulder Joint Loads During Activities of Daily Living," Journal of Biomechanics 42 (2009), pp. 1840-1849. (10 pages).
Williams, Gerald R., Jr., M.D., and Iannotti, Joseph P., M.D. PhD., "Options for Glenoid Bone Loss: composites of Prosthetics and Biologics," Journal of Shoulder and Elbow Surgery, Sep./Oct. 2007, vol. 16, No. 5S, pp. 267S-272S. (6 pages).
Wirth, Michael A., M.D. and Rockwood, Charles A., Jr., M.D., "Complications of Shoulder Arthroplasty," Clinical Orthopaedics and Related Research, Oct. 1994, No. 307, pp. 47-69. ( 23 pages).
Wirth, Michael A. and Rockwood, Charles A., Jr., "Current Concepts Review—Complications of Total Shoulder-Replacement Arthroplasty," Journal of Bone & Joint Surgery, Apr. 1996, vol. 78-A, No. 4, pp. 603-616. (15 pages).
Frederick et al., "Shoulder Arthroplasty: The Socket Perspective," J Shoulder Elbow Surg. 2007; 16:241S-247S.
Antuna et al., "Glenoid revision surgery after total shoulder arthroplasty," Journal of Shoulder Elbow Surgery, 2001, pp. 217-224, vol. 10, Rochester, MN (8 pages).
Boileau P, Walch G., "The three dimensional geometry of the proximal humerus. Implications for the surgical technique and prosthetic design." J. Bone Joint Surg Br 1997;79-B:857-65, doi:10.1302/0301-620X.79B5.7579 (9 pages).
Boyer PJ, Massimini DF, Gill TJ, Fapannagari R, Stewart SL, Warner JP, Li G., "In vivo articular cartilage contact at the glenohumeral joint: preliminary report." J. Orthop Sci. 2008;13:359-65.doi:10.1007/s00776-008-1237-3 (7 pages).
Bryce CD, Davison AC, Lewis GS, Wang, Flemming DJ, Armstrong AD., "Two dimensional glenoid version measurements vary with coronal and sagittal scapular rotation." J Bone Joint Surg Am. 2010;92-692-9.doi.10.2106/JBJS.I.00177 (8 pages).
Codsi et al., "Normal glenoid vault anatomy and validation of a novel glenoid implant shape," Journal of Shoulder Elbow Surgery, May/Jun. 2008, pp. 471-478, vol. 17, Austria (8 pages).
Couteau B, Mansat, Darmana R, Mansat M., Egan J., "Morphological and mechanical analysis of the glenoid by 3D geometric reconstruction using computed tomography." Clin Biomech 2000;15(suppl1):8-12.doi:10.1016/S0268-0033 (00)00052-8 (5 pages).

(56) References Cited

OTHER PUBLICATIONS

Couteau B, Mansat P. Estivales E, Darmana R. Mansat M., Egan J., "Finite element analysis of the mechanical behavior of a scapula implanted with a glenoid prosthesis." Clin Biomech 2001;16:566-75,doi:10.1016/S0268-0033(01) 00029-8 (10 pages).

Couteau B, Mansat P, Mansat M, Darmana R, Egan J., "In vivo characterization of glenoid with use of computed tomography." J Shoulder Elbow Surg 2001:116-22 (7 pages).

De Wilde LF, Verstraetern T, Speeckaert W, Karelse A., "Reliability of the glenoid plane." J Shoulder Elbow Surg. 2010:19:414-22. doi:10.1016/j.jse.2009.10.005. (9 pages).

Graichen H, Hinterwimmer S, von Eisenhart-Rothe R, Vogl T. Engimeier KH, Eckstein F., "Effect of abducting and adducting muscle acitivity on glenohumeral translation, scapular kinematics and subacromial space width in vivo." Journal of Biomechanics 2005;38:755-60. doi:10.1016/j.jbiomech.2004.05.020. (6 pages).

Graichen H, Stammberger T. Bonel H, Karl-Hans E, Reiser M, Eckstein F., "Glenohumeral translation during active and passive elevation of the shoulder—a 3D open-MRI study," Journal of Biomechanics 2000;33:609-13.doi:10.1016/S0021-9290(99)00209-2. (5 pages).

Harryman DT, Sidles JA, Harris SL, Lippitt SB, Matsen FA., "The effect of articular conformity and the size of the humeral head component on laxity and motion after glenohumeral arthroplasty," J. Bone Joint Surg Am 1995;77-A:555-63,No doi found. (10 pages).

Huysmans PE, Haen PS, Kidd M, Dhert WJ, Willems JW., "The shape of the inferior part of the glenoid: a cadaveric study." J Shoulder Elbow Surg. 15(6):759-63. doi:10.1016/j.jse.2005.09.001 (5 pages).

Karelse et al., "The Pillars of the Scapula", Clinical Anatomy, 2007, pp. 392-399, vol. 20, Belgium (8 pages).

\* cited by examiner

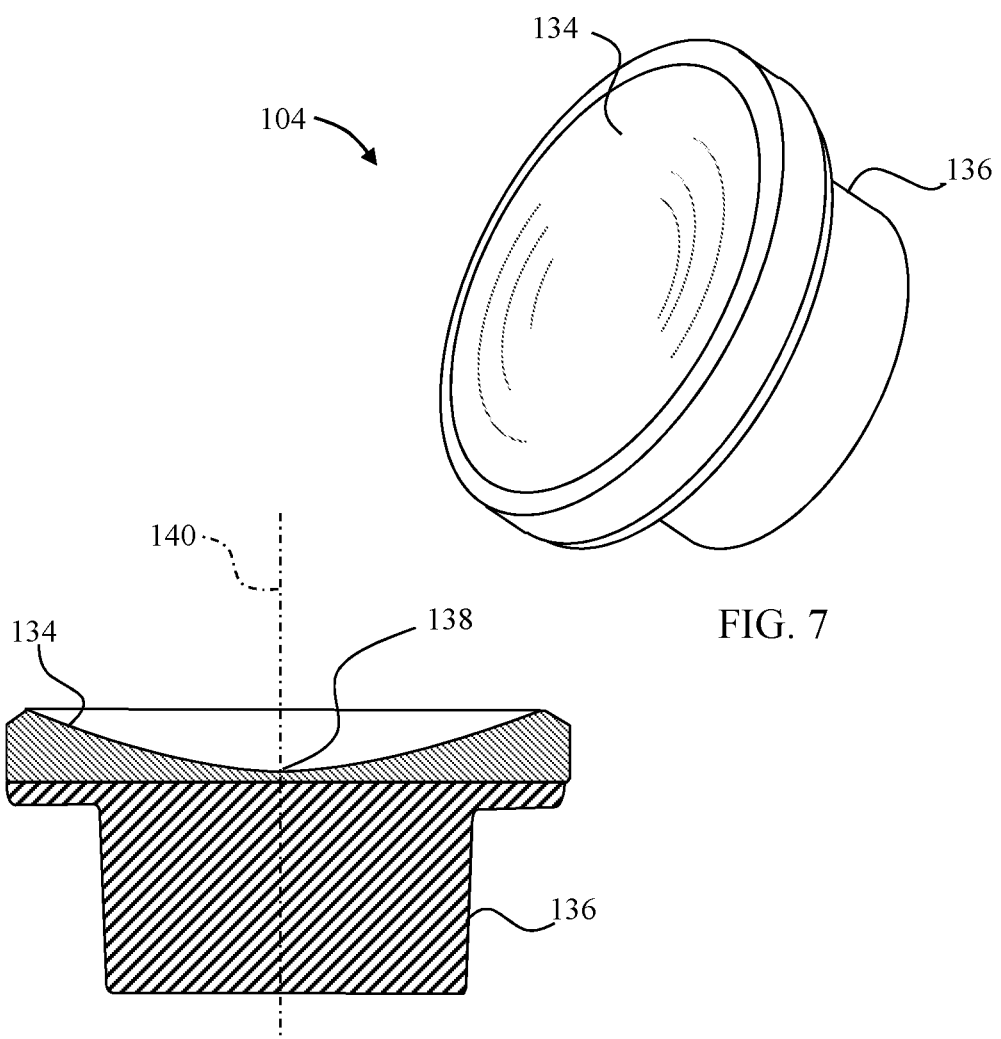
FIG. 7
FIG. 8
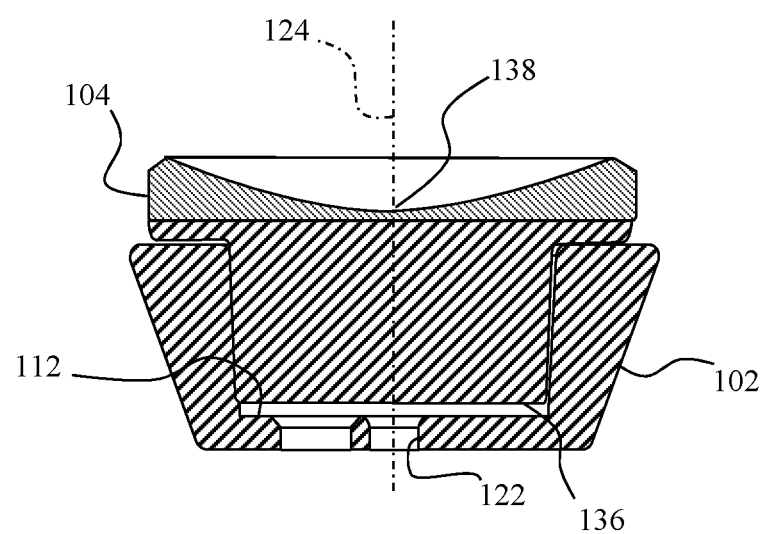
FIG. 9

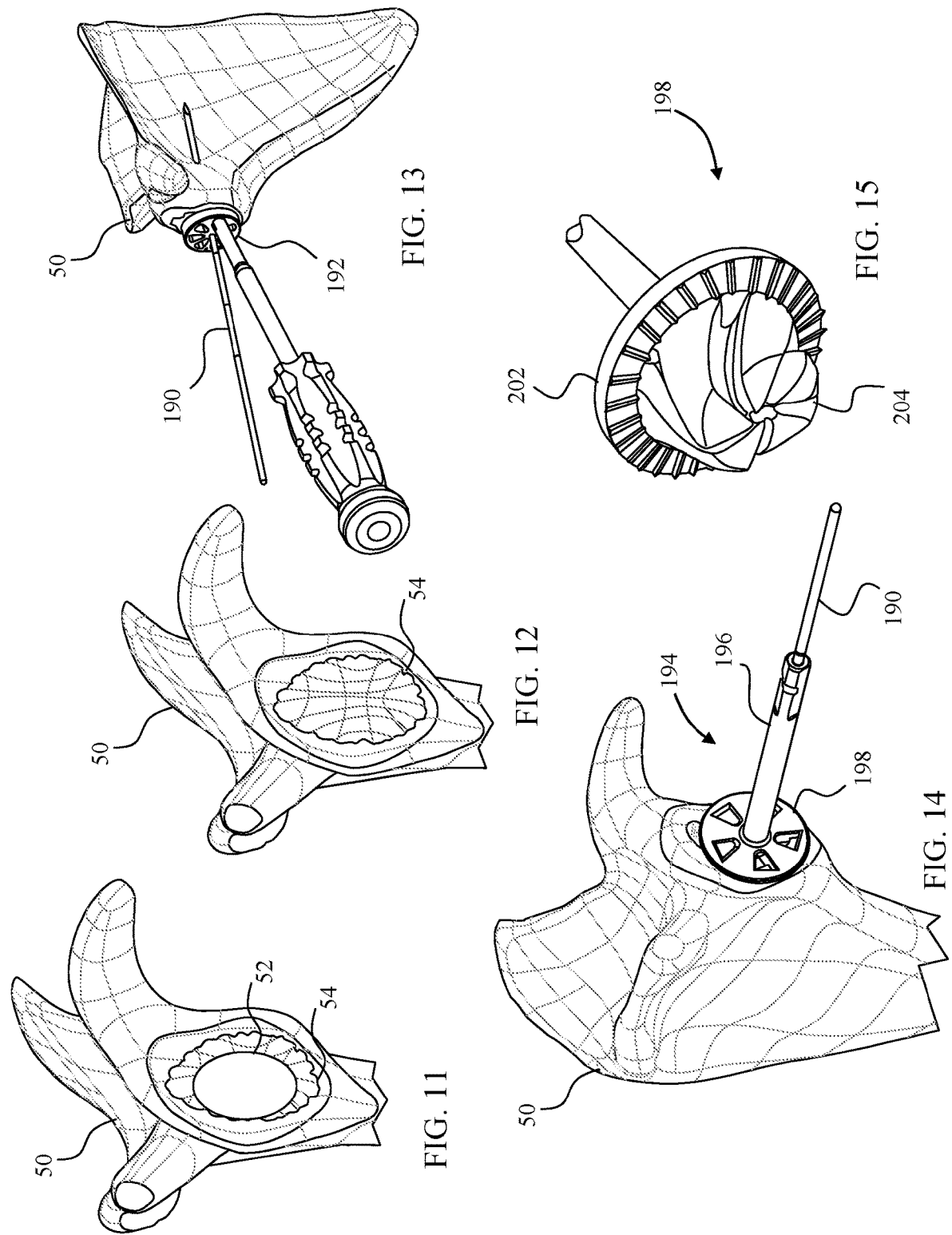

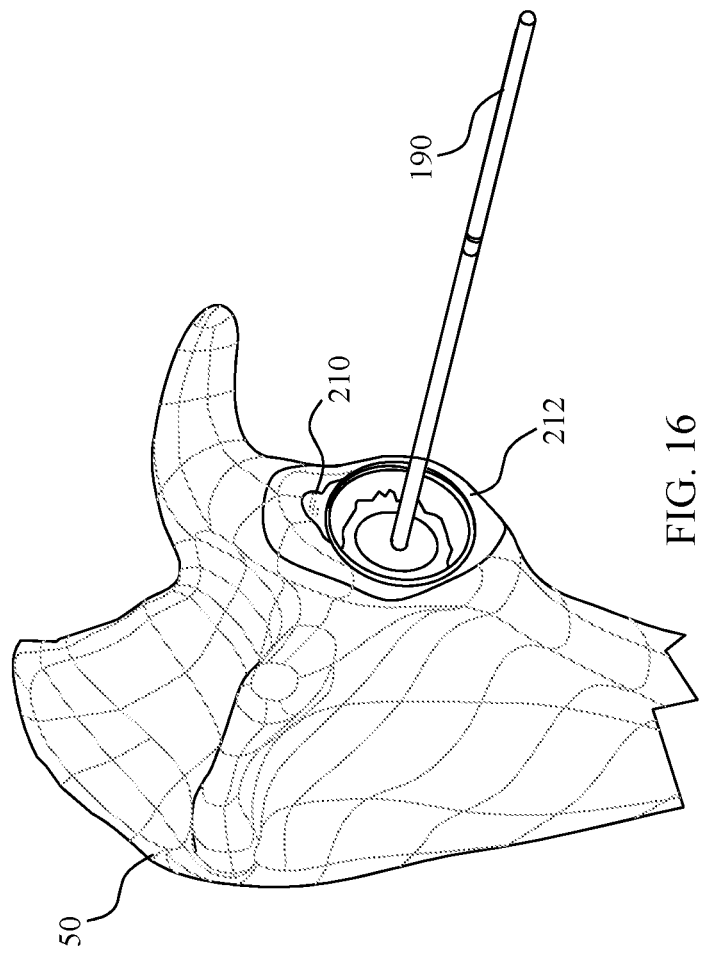
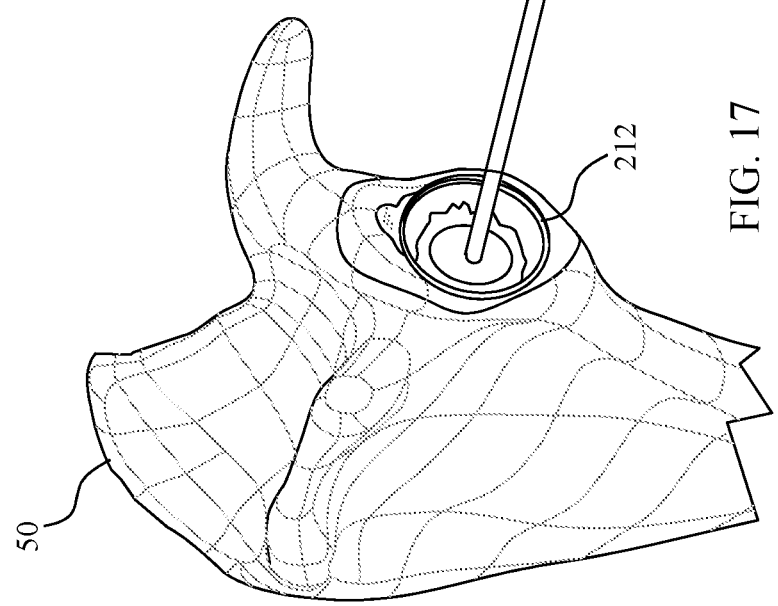

under the U.S. 11,076,963 B2

REVISION GLENOID DEVICE

CROSS-REFERENCE TO RELATED APPLICATIONS

This is a divisional application of U.S. application Ser. No. 14/027,907, filed on Sep. 16, 2013, now U.S. Pat. No. 10,172,715 which issued Jan. 8, 2019 and which is a divisional application of U.S. application Ser. No. 13/051,062, filed on Mar. 18, 2011, now U.S. Pat. No. 8,551,177 which issued Oct. 8, 2013, the entire disclosures of which are incorporated herein by reference, which references U.S. patent application Ser. No. 13/051,011, entitled "Circular Glenoid Method for Shoulder Arthroscopy", which was filed on Mar. 18, 2011, U.S. patent application Ser. No. 13/051,026, entitled "Combination Reamer/Drill Bit for Shoulder Arthroscopy", which was also filed on Mar. 18, 2011, and U.S. patent application Ser. No. 13/051,041, entitled "Device and Method for Retroversion Correction Cone for Shoulder Arthroscopy", which was also filed on Mar. 18, 2011, the contents of which are each incorporated herein by reference.

TECHNICAL FIELD OF THE INVENTION

The present invention relates generally to the field of orthopedics, and, more particularly, to glenoid component apparatuses for shoulder arthroplasty and methods for using them.

BACKGROUND

As depicted in FIG. 1, a typical shoulder or glenohumeral joint is formed in a human body where the humerus 10 movably contacts the scapula 12. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa 14 and suitably resecting cancellous bone 22 from the glenoid vault 20.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical and positioning of the humeral component is accomplished by using the anatomical neck of the humerus as the reference plane for reconstruction of the humeral head.

In known systems, the glenoid component is positioned in the geometric center of the glenoid fossa. The geometric center is established by generating a line from the most superior point of the glenoid rim to the most inferior point of the glenoid rim ("Saller's line"). A second line is generated between the most posterior point of the glenoid rim and the most anterior point of the glenoid rim. The intersection of the two generated lines is considered to be the geometric center of the area circumscribed by the glenoid rim. By way of example, FIG. 2 depicts a sagittal view of the scapula 12. In FIG. 2, Saller's line 30 extends between the most superior point 32 of the glenoid rim 24 and the most inferior point 34 of the glenoid rim 24. A second line 36 extends from the most posterior point 38 of the glenoid rim 24 and the most anterior point 40 of the glenoid rim. The geometric center 42 of the glenoid fossa 14 is located at the intersection of the line 36 and Saller's line 30. As used herein, the terms anterior, posterior, superior, and inferior, unless otherwise specifically described, are used with respect to the orientation of the scapula 12 as depicted in FIG. 2.

Over time, implanted glenoid components can become loosened. Loosened components can result in increased pain for an individual. Correction of the problem, however, may be problematic. For example, replacement of components which are loosened may be complicated by a number of different glenoid deficiencies. Glenoid deficiencies may be classified as central (a void area in the central region of the glenoid fossa), peripheral (a void area in the glenoid rim area), or combined (a void area extending from the central region of the glenoid fossa to the glenoid rim area). Replacement of components in the presence of mild or moderate deficiencies, particularly when limited to the central region, may be accomplished using known components with or without bone grafting to fill remaining void areas. In cases involving large central deficiencies and combined deficiencies, however, other procedures such as allografting are required. Once the grafted material has been incorporated into the glenoid, a second surgery is performed to implant a replacement component into the allograft.

An alternative to grafting procedures is customization of components for the particular patient deficiency. Of course, customization increases the costs for a given procedure. Moreover, obtaining reproducible results is difficult when each procedure is unique.

There remains a need for a glenoid component that allows for establishing normal kinematics in revision procedures. There is a further need for a technique, instrumentation, and implant that facilitates positioning of such a component even when the glenoid has a variety of deficiencies. A glenoid component that can be positioned in a manner that reduces the amount of bone that is required to be removed without overly complicating the implant procedure is also needed.

SUMMARY OF THE INVENTION

The present invention in one embodiment provides a method of implanting a revision glenoid component including accessing a previously implanted glenoid component in a scapula, removing the previously implanted glenoid component, identifying an inferior glenoid circle center of the scapula, preparing a glenoid fossa of the scapula to receive a revision glenoid component, selecting a revision glenoid component, and implanting the selected revision glenoid component based upon the identified inferior glenoid circle center in the prepared glenoid fossa.

In another embodiment, a method of implanting a revision glenoid component includes obtaining an image of a scapula, identifying an inferior glenoid circle center of the scapula based upon the image, selecting a revision glenoid component, removing a previously implanted glenoid component from the scapula, preparing a glenoid fossa of the scapula to receive a prosthesis, and implanting the selected revision glenoid component in the prepared glenoid fossa based upon the identified inferior glenoid circle center.

In a further embodiment a glenoid component includes a base component with a planar upper circular rim defining a first plane, a receptacle opening to the first plane, a lower planar circular surface defining a second plane parallel to the first plane, and a conical outer wall extending from the upper circular rim to the lower planar circular surface. The glenoid component includes an articulating component with an upper articulating surface and a lower coupling portion configured to be inserted into the receptacle.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 7 depicts a front perspective view of the articulating component of the retroversion glenoid component of FIG. 3;

FIG. 8 depicts a side cross-sectional view of the articulation component of the retroversion glenoid component of FIG. 3;

FIG. 9 depicts a side cross-sectional view of the retroversion glenoid component of FIG. 3;

FIG. 11 depicts a sagittal view of a scapula with an implanted glenoid component which exhibits severe central bone loss resulting in undesired movement of the implanted glenoid component and which has been accessed in accordance with the procedure of FIG. 10;

FIG. 12 depicts a sagittal view of the scapula of FIG. 11 after the previously implanted glenoid component has been removed;

FIG. 13 depicts a front perspective view of the scapula of FIG. 11 with a guide pin placement guide positioned to guide placement of the guide pin such that the guide pin is aligned with the glenoid axis of the scapula;

FIG. 14 depicts a side perspective view of the guide pin of FIG. 13 used to guide a combined reaming/planning device that may be included in a kit;

FIG. 15 depicts a partial bottom perspective view of the combined reaming/planning device of FIG. 14 showing a planning portion and a reaming portion;

FIG. 16 depicts a side perspective view of the scapula of FIG. 14 after a cavity has been reamed and after the glenoid has been repaired by using bone graft and a compactor to replace bone loss areas about the cavity;

FIG. 17 depicts the side perspective view of the scapula of FIG. 16 with the guide hole of a base component aligned with the guide pin such that the base component will be positioned in alignment with the glenoid axis of the scapula;

DETAILED DESCRIPTION

Figure 1:
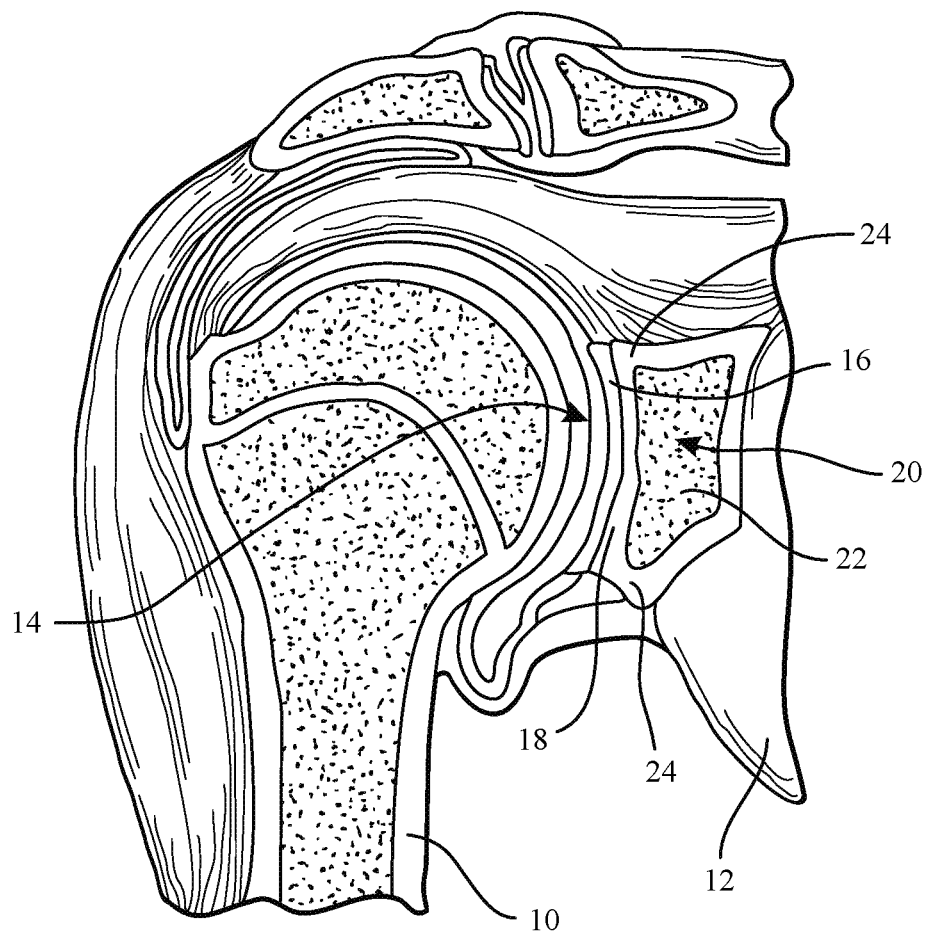
FIG. 1 depicts a coronal view of an anatomically normal shoulder joint.
Figure 2:
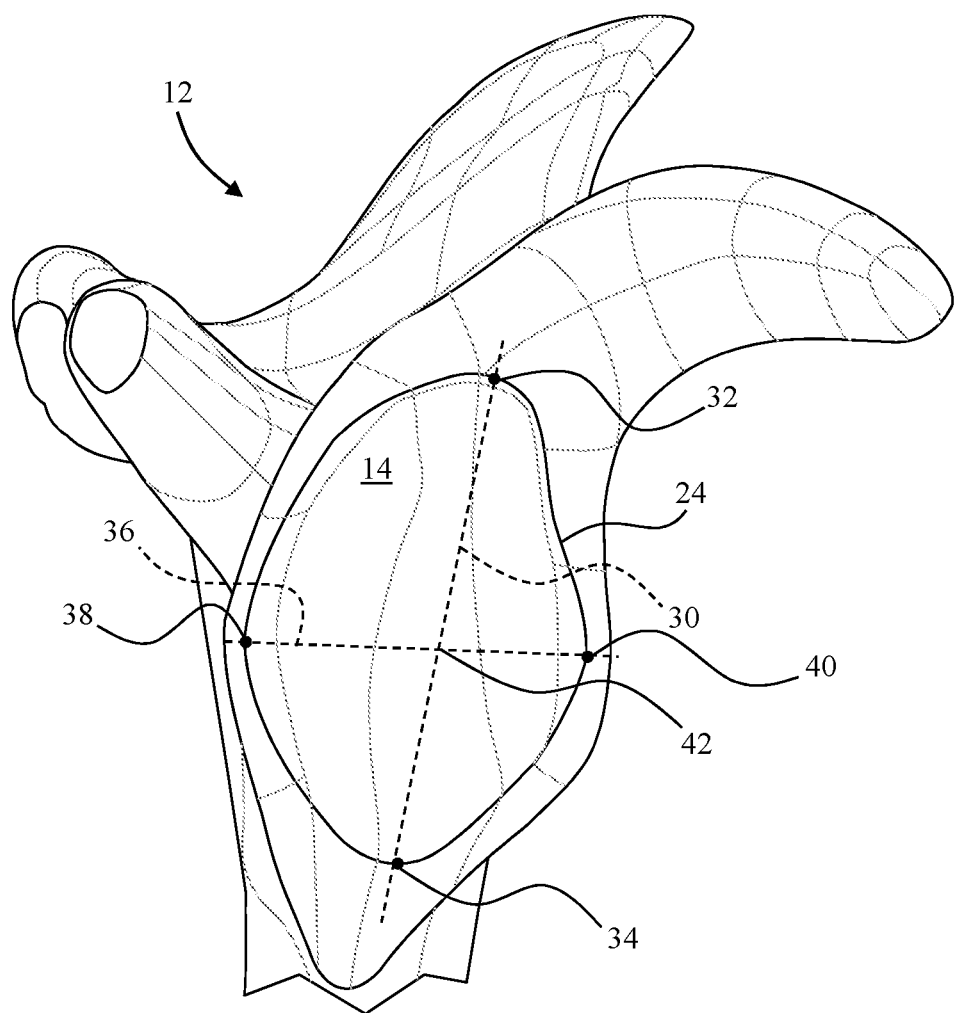
FIG. 2 depicts a sagittal view of the shoulder joint of FIG. 1.

Like reference numerals refer to like parts throughout the following description and the accompanying drawings.

Figure 3:
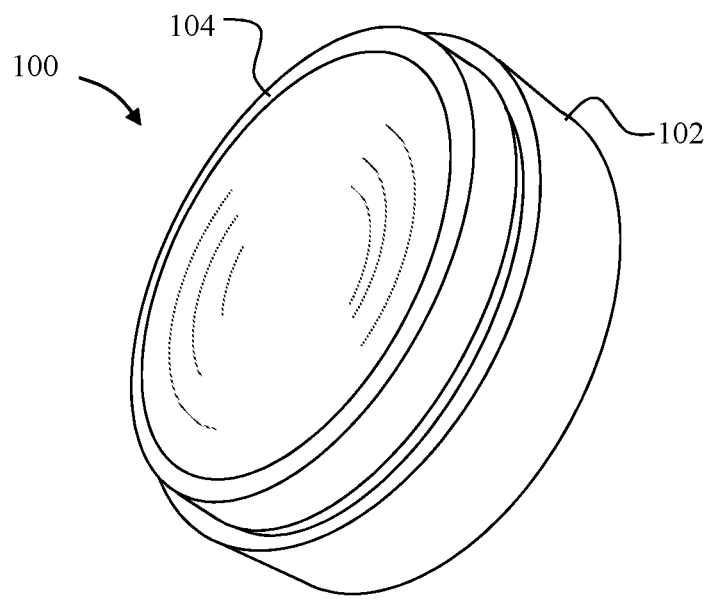
FIG. 3 depicts a front perspective view of a retroversion glenoid component that may be implanted in a scapula in accordance with principles of the invention.
Figure 4:
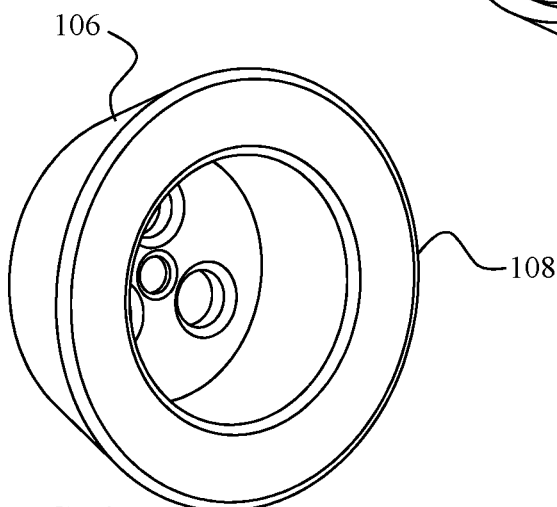
FIG. 4 depicts a front perspective view of the base of the retroversion glenoid component of FIG. 3 that may be implanted in a scapula in accordance with principles of the invention.
Figure 5:
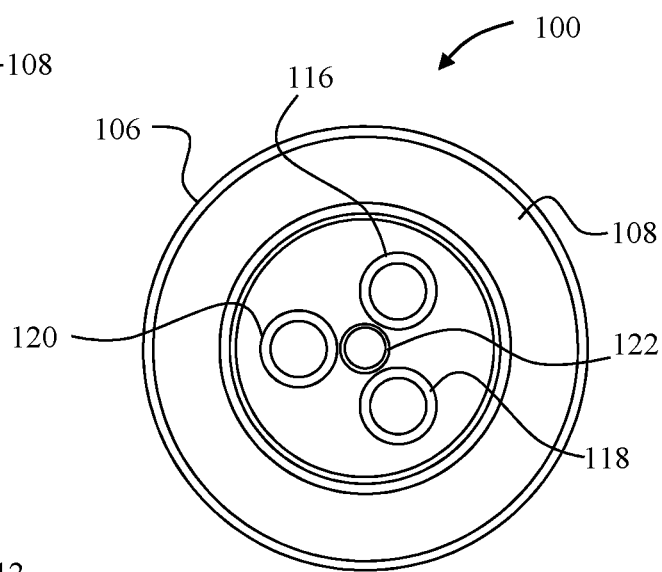
FIG. 5 depicts a top plan view of the base of the retroversion glenoid component of FIG. 3.
Figure 6:
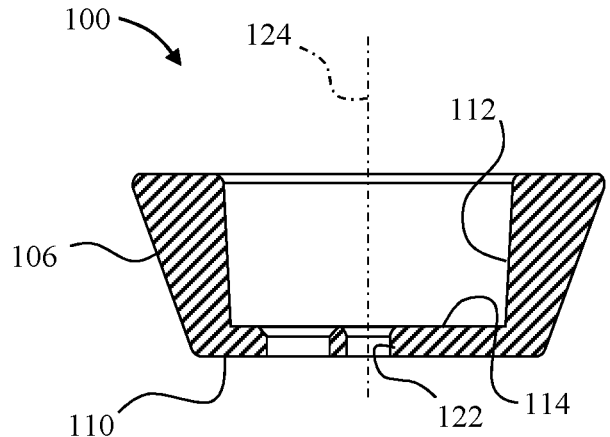
FIG. 6 depicts a side cross-sectional view of the base of the retroversion glenoid component of FIG. 3.

FIG. 3 depicts a retroversion glenoid component 100. The glenoid component 100 includes a base component 102 and an articulation component 104. With further reference to FIGS. 4-6, the base component 102 includes a wall 106 which extends between a lip 108 and a bottom surface 110. At the lip 108, the wall 106 defines a circular outer periphery that is slightly larger than the circular outer periphery of the wall 106 at the bottom surface 110.

The lip 108 defines a receptacle 112 which is substantially cylindrical. The receptacle 112 extends from the lip 108 to a lower surface 114. Three fastener holes 116, 118, and 120 extend through the lower surface 114 and the bottom surface 110. A guide hole 122 also extends through the lower surface 114 and the bottom surface 110. The guide hole 122 and the receptacle 112 are centrally located. Accordingly, the guide hole 122, the receptacle 112, and the outer wall 106 define a unitary axis 124.

The articulating component 104, depicted in FIGS. 6 and 7, includes a spherical articulating surface 134 and a coupling portion 136. The coupling portion 136 is substantially cylindrical in shape and sized with a diameter slightly larger than the diameter of the receptacle 112. The articulating surface is positioned with a nadir 138 located on a central axis 140 of the articulating component 104. Accordingly, when the articulation component 104 is coupled with the base component 102 as depicted in FIG. 9, the nadir 138 is located on the axis 124 of the base component.

The glenoid component 100 in this embodiment is modular, but in other embodiments may be integrally formed. Integrally formed units may be made from a durable biocompatible plastic or any other suitable durable biocompatible material. For example, the glenoid component 100 may be made from a polyethylene. One particular polyethylene that is well suited for glenoid component 100 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference.

In the embodiment of FIG. 3 wherein the articulation component 104 and the base component 102 are separately formed, the various components may be made from different materials. Thus, the articulating surface 134 may be made from UHMWPE, while the coupling portion 136 and the base component 102 may be made from a suitable biocompatible metal such as, for example, a cobalt chromium alloy, a stainless steel alloy, a titanium alloy, or any other suitable durable material. In this embodiment, the articulating surface 134 is secured to the coupling portion 136 in any suitable manner. For example, articulating surface 134 may be bonded to coupling portion 136, or articulating surface 134 could be made from polyethylene and compression molded to coupling portion 136. Alternately, the articulating surface 134 may be glued to the coupling portion 136, for example, an adhesive. Alternatively, articulating surface 134 may be mechanically interlocked to the coupling portion 136 by taper locking or otherwise press-fitting the articulating surface 134 into the coupling portion 136 and the coupling portion 136 may include any other suitable interlocking features, for example, rib(s), lip(s), detent(s), and/or other protrusion(s) and mating groove(s), channel(s), or indent(s) (not shown).

In alternative embodiments, one or more of the outer wall 106 and the bottom surface 110 may include a porous coating to facilitate bone in-growth into the glenoid component 100. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference.

The glenoid component 100 may be included in a kit incorporating instrumentation that may be used to facilitate implantation of the glenoid component 100. Such instrumentation may include reamers and guide pins, as discussed more fully below. Additionally, the kit may include base components having different heights and widths. Typical heights may range between 10 and 30 millimeters (mm). The kit may further include articulation components having different diameters. In one embodiment, a kit includes articulation components having a variety of diameters ranging from about 23 mm to about 30 mm.

Preferably, each of the base components in a kit has a receptacle 112 that is shaped and dimensioned the same as the receptacle 112 of each of the other base components 102 while each of the articulation components 104 has a coupling portion 136 that is shaped and dimensioned the same as the coupling portion 136 of each of the other articulation components 104. Accordingly, any of the articulation components 104 may be coupled with any of the base components 102 in the kit.

Figure 10:
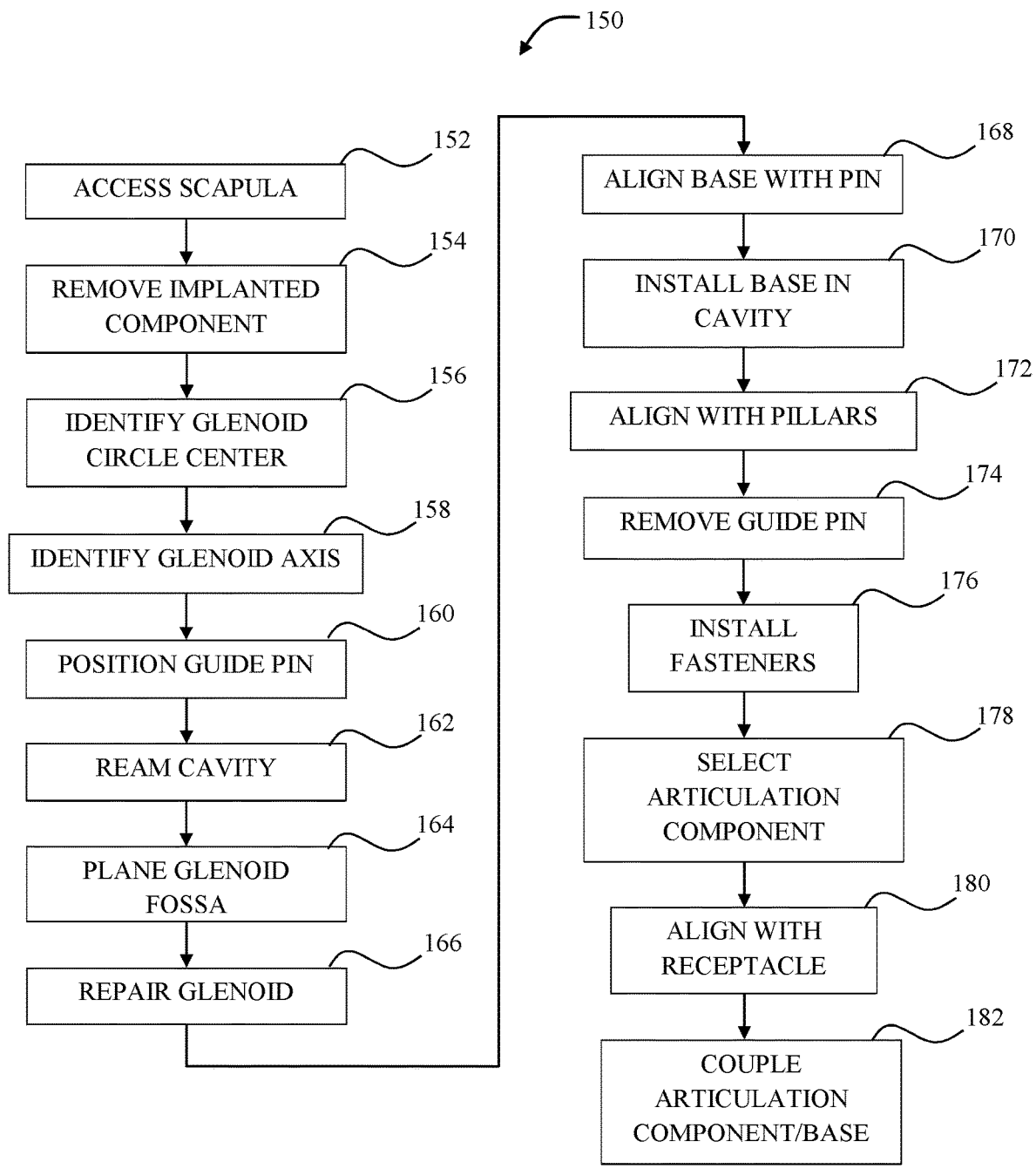
FIG. 10 depicts a medical procedure that may be used to implant the retroversion glenoid component base of FIG. 3 into a scapula using a kit that includes a guide pin and a combined reaming/planing tool.

A kit including the glenoid component 100 may be used to implant the glenoid component 100 into a scapula that has previously received a glenoid component in accordance with a procedure 150 depicted in FIG. 10. In accordance with the procedure 150, a scapula is accessed at block 152 in accordance with a desired surgical approach. The previously implanted glenoid component is then removed at block 154. At block 156, the center of an inferior glenoid circle, further described in co-pending U.S. patent application Ser. No. 13/051,011, is identified for the scapula. While visual identification of the inferior glenoid circle and hence the center of the inferior glenoid circle is possible once the scapula is accessed at block 152, the center of the inferior glenoid circle may alternatively be identified prior to or after incising a patient with the aid of imaging or other techniques.

Once the center of the inferior glenoid circle is identified at block 156, a glenoid axis which extends through the center of the inferior glenoid circle and is perpendicular to the articulating surface of the glenoid is identified (block 158). In alternative approaches, the glenoid axis may extend through the scapula at locations other than the center of the inferior glenoid circle. The glenoid axis may be identified prior to or after incising a patient with the aid of imaging or other techniques.

Next, a guide pin is positioned in the scapula such that the longitudinal axis of the guide pin is coextensive with the glenoid axis (block 160). A circular cavity is then reamed in the glenoid (block 162) and the glenoid surface is planed (block 164). The circular cavity is preferably slightly larger than the diameter of the revision glenoid base component 102. This allows for positioning of the base component 102 without placing stress on the glenoid which may be significantly compromised as discussed more fully below. At block 166, a bone graft compactor is used over the guide pin, if needed, to fill in void areas of the glenoid which are not needed for receiving the revision glenoid component. The guide hole 122 of the base component 102 is then aligned with and inserted onto the guide pin (block 168).

Using the guide pin as a guide, the base component 102 is then implanted in the prepared glenoid (block 170). Because the guide pin is positioned on the glenoid axis and because the guide pin is positioned within the guide hole 122, using the guide pin ensures that the central axis 124 of the base component (see FIG. 6) is aligned with the glenoid axis. At block 172, the base component 122 may further be rotated about the guide pin to align one or more of the fastener holes 116, 118, and 120 with a respective one of the pillars of the scapula as described by A. Karellse, et al., "Pillars of the Scapula", *Clinical Anatomy*, vol. 20, pp. 392-399 (2007). Typically, at least two of the fastener holes 116, 118, and 120 may be positioned so as to access the lateral and spina pillars. Rotation of the base component 102 is facilitated since the cavity in the glenoid is slightly larger than the base component 102 as discussed above.

The guide pin may then be removed (block 174) and one or more fasteners may be inserted through fastener holes 116, 118, and 120 to affix the base component 102 to the scapula (block 176). To ensure firm fixation of the base component 102, it is preferred that one or even two fasteners extend into solid bone material within one or more of the pillars of the scapula. The fastener holes 116, 118, and 120 may be configured to allow for variable angle fastener placement to assist in achieving a firm fixation. A desired articulation component is then obtained (block 178) and the coupling portion 136 is aligned with the receptacle 112 (block 180). The coupling portion 136 is then moved into the receptacle 112 and the articulation component 104 is coupled to the base component 102 (block 182). Coupling may be facilitated by forming the coupling portion 136 and the receptacle 112 to form a friction fit, Morse taper, etc. Once the articulation component 104 is coupled to the base component 102, the nadir 138 will be aligned with the glenoid axis since the articulation component 104 is configured to couple with the base component 102 such that the nadir 138 is on the axis 140 as discussed above.

FIGS. 11-20 depict a scapula 50 at various points of the procedure 220. In FIG. 11, the scapula 12 is depicted after block 152 with a previously implanted glenoid component 52. FIG. 12 depicts the scapula 50 after the component 52 has been removed. The scapula 50 in FIG. 12 exhibits severe central bone loss which has resulted in instability of the glenoid component 52. The methods and devices disclosed herein may be used in performing a retroversion glenoid implantation in the presence of a variety of glenoid deficiencies including central, peripheral, and combined deficiencies ranging from mild to severe. Because the base component 102 is not press fit in to the scapula as discussed above, the potential of fracturing a portion of the scapula even in the presence of severe deficiencies is reduced.

FIG. 13 depicts a guide pin 190 and a guide pin placement guide 192 that may be included in a kit used to perform a revision glenoid component implantation procedure. The guide pin placement guide 192 is positioned on the scapula 50 substantially centered upon the inferior glenoid circle. The guide pin 190 is thus positioned in the scapula 50 with the longitudinal axis of the guide pin 190 aligned with the glenoid axis.

FIG. 14 depicts the scapula 50 with the guide pin 190 used to guide a combination reaming device 194 that may also be included in a kit in accordance with the present disclosure. The combination reaming device 194 includes a shaft 196 and a working portion 198. The shaft 196 and the working portion 198 are cannulated to allow the guide pin 190 to be used to precisely position the combination device 194. The working portion 198 includes an outer planing portion 202 and a central reaming portion 204. The planing portion 202 and the central reaming portion 204 allow for simultaneous reaming and planing of the glenoid surface. Alternatively, two separate devices may be used sequentially.

Once the scapula 50 has been reamed and planed, some areas of deficiency may be present. Accordingly, bone grafting material may be used to fill the void areas. In one embodiment, a kit includes a cannulated compactor which is shaped like the reaming portion 204. The cannulated compactor may be guided by the guide pin 190 to compact bone graft material 210 (see FIG. 16) while maintaining or finally forming a cavity 212 that is shaped slightly larger than the outer wall 106 of the base component 102.

Figure 18:
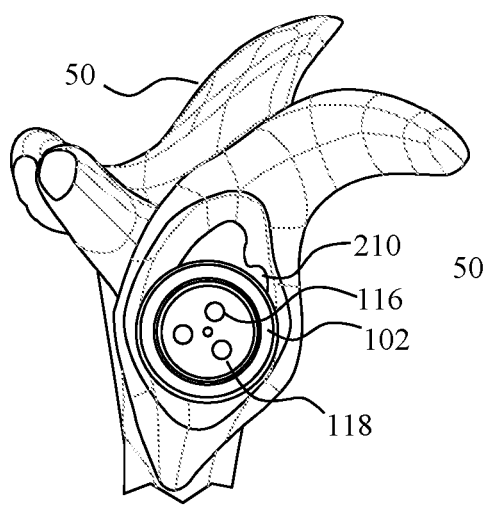
FIG. 18 depicts a sagittal plan view of the scapula of FIG. 17 with the base component rotated such that fasteners inserted into two of the fastener holes of the base can access a lateral pillar and a spina pillar of the scapula.

The guide hole 202 is then aligned with the guide pin 190 as depicted in FIG. 17 and the base component 102 is guided by the pin 190 into the cavity 212. The base component 102 is then rotated within the cavity 212 as desired to position the fastener holes 116, 118, or 120 to allow a fastener passed therethrough to be fixed into solid bone. By way of example, FIG. 18 depicts the base component 102 positioned such that a fastener passing through the fastener hole 116 may be fixed in the lateral pillar while a fastener passing through the fastener hole 118 may be fixed in the spina pillar. Thus, even though some or all of the base component 102 may be positioned on bone graft 210 (see, e.g., FIG. 19), the base component may be solidly fixed to the scapula 50. Thus, even when bone graft material 210 is used to fill in deficient areas of the scapula 50, a second surgery is not required.

Figure 19:
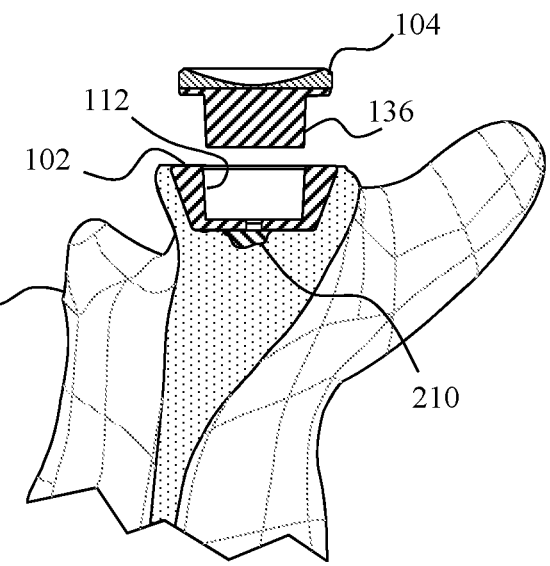
FIG. 19 depicts a cross-sectional view of the scapula of FIG. 18 with the coupling portion of the selected articulation component aligned with the receptacle of the base component.
Figure 20:
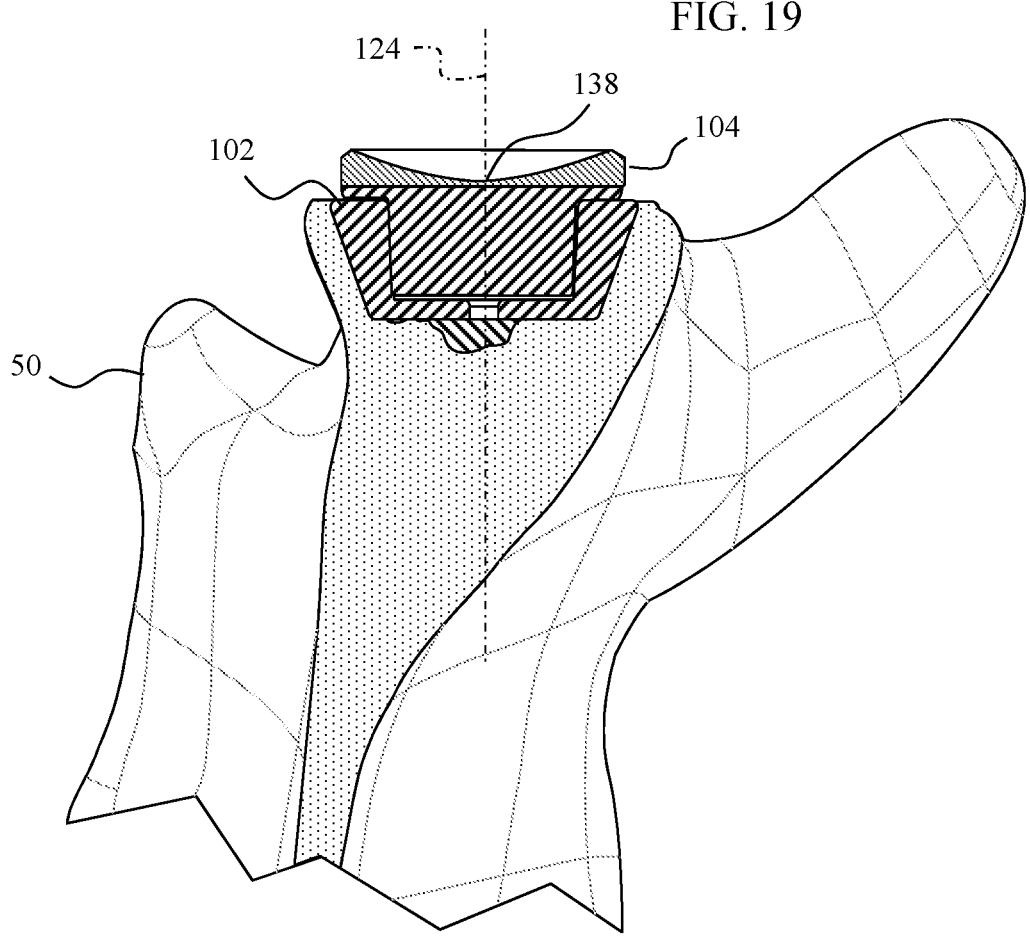
FIG. 20 depicts a cross-sectional view of the scapula of FIG. 19 with the articulation component coupled with the base component such that the nadir of the articulation component is positioned at the glenoid axis of the scapula.

Once the base 102 is fixed to the scapula 50 and the guide pin 190 is removed, in any desired sequence, the coupling portion 136 of the selected articulation component 104 is aligned with the receptacle 112 of the base component 102 as depicted in FIG. 19. The coupling portion 136 is then moved into the receptacle 112 and the articulation component 104 is coupled to the base component 102 in any desired manner, such as by a Morse taper fit between the coupling portion 136 and the receptacle 112, resulting in the configuration of FIG. 20. In FIG. 20, the nadir 138 is located on the glenoid axis since the base component 102 was fixed with the axis 124 of the guide hole 122 aligned with the glenoid axis as discussed above.

While the foregoing examples detailed only a single glenoid component 100, a kit may incorporate a number of different glenoid components. Each glenoid component in the kit may be of a different diameter. Additionally, the procedure 150 may be modified in a number of ways in addition to those discussed above. By way of example, while in the above example the glenoid component 100 was implanted with the nadir 138 aligned with the inferior glenoid circle center at block 182, the nadir 138 may alternatively be offset from the inferior glenoid circle center. For example, the nadir 138 may be offset from the inferior glenoid circle center by about 1.1 mm in a direction superiorly and posteriorly from the inferior glenoid circle center by positioning the guide pin 190 at the offset location at block 160. Imaging and computer based systems may be used to assist in the positioning of the glenoid component at this location.

Moreover, while a specific sequence was described in the procedure 150, many of the steps may be performed in a different order and/or simultaneously with other of the steps.

In accordance with the methods described above, a glenoid component with a spherical articulating surface is implanted at or very near to the spinning point of a shoulder in a revision procedure. Because of the location of the glenoid component, a humeral component with a radius of curvature matched to the radius of curvature of the articulating surface may be used to provide a constrained fit. As used herein, the term "matched" means a difference in the radii of curvature of the articulating surfaces of less than 2 mm.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A glenoid component, comprising:
 a base component including a planar upper circular rim defining a first plane, a receptacle opening to the first plane, a lower planar circular surface defining a second plane parallel to the first plane, and a conical outer wall extending from the upper circular rim to the lower planar circular surface; and
 an articulating component, the articulating component including
  an upper articulating surface,
  a lower coupling portion including a first portion configured to be inserted into the receptacle so as to be completely beneath the first plane, and
  an outwardly extending portion extending outwardly from the first portion along the first plane and located between the first portion and the upper articulating surface, the outwardly extending portion configured to be completely above the first plane when the first portion is inserted into the receptacle,
 wherein:
  the base component defines a maximum base component diameter along the first plane;
  the articulating surface defines a maximum articulating surface diameter along the first plane;

the outwardly extending portion defines a maximum outwardly extending portion diameter along the first plane;

the maximum outwardly extending portion diameter is greater than the maximum articulating surface diameter; and the maximum base component diameter is greater than the maximum outwardly extending portion diameter.

2. The glenoid component of claim 1, wherein:

the base component has a first maximum height in a direction perpendicular to the first plane;

the receptacle has a maximum receptacle diameter along the first plane; and the maximum receptacle diameter is greater than the first maximum height.

3. The glenoid component of claim 2, wherein:

the articulating component has a second maximum height in the direction perpendicular to the first plane when the articulating component is inserted into the receptacle; and the maximum receptacle diameter is greater than the second maximum height.

4. The glenoid component of claim 3, further comprising:

a guide hole extending from the receptacle to the lower planar circular surface.

5. The glenoid component of claim 4, further comprising:

a plurality of fastener holes extending from the receptacle to the lower planar surface.

6. The glenoid component of claim 2, further comprising:

a guide hole extending from the receptacle to the lower planar circular surface.

7. The glenoid component of claim 6, further comprising:

a plurality of fastener holes extending from the receptacle to the lower planar surface.

8. The glenoid component of claim 2, wherein:

the maximum receptacle diameter is greater than a combined maximum height of a combination of the articulating component and the base in a direction perpendicular to the first plane when the articulating component is inserted into the receptacle.

9. The glenoid component of claim 1, wherein:

a maximum diameter of the conical outer wall is greater than a maximum height of the articulating component in a direction perpendicular to the first plane when the articulating component is inserted into the receptacle.

10. The glenoid component of claim 9, further comprising:

a guide hole extending from the receptacle to the lower planar circular surface; and a plurality of fastener holes extending from the receptacle to the lower planar surface.

11. The glenoid component of claim 1, further comprising:

a guide hole extending from the receptacle to the lower planar circular surface; and a plurality of fastener holes extending from the receptacle to the lower planar surface.

* * * * *